(12) United States Patent
Krijn et al.

(10) Patent No.: US 9,392,753 B2
(45) Date of Patent: Jul. 19, 2016

(54) HORTICULTURE LIGHTING INTERFACE FOR INTERFACING AT LEAST ONE LIGHTING SYSTEM

(71) Applicant: KONINKLIJKE PHILIPS N.V., Eindhoven (NL)

(72) Inventors: Marcellinus Petrus Carolus Michael Krijn, Eindhoven (NL); Henricus Marie Peeters, Eindhoven (NL); Esther Maria Van Echtelt, Eindhoven (NL); Marc Andre Peters, Eindhoven (NL); Cristina Tanase, Eindhoven (NL); Gabriel-Eugen Onac, Eindhoven (NL); Celine Catherine Sarah Nicole, Eindhoven (NL); Rob Franciscus Maria Van Elmpt, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/653,548

(22) PCT Filed: Dec. 17, 2013

(86) PCT No.: PCT/IB2013/061024
§ 371 (c)(1),
(2) Date: Jun. 18, 2015

(87) PCT Pub. No.: WO2014/097138
PCT Pub. Date: Jun. 26, 2014

(65) Prior Publication Data
US 2015/0342125 A1 Dec. 3, 2015

Related U.S. Application Data

(60) Provisional application No. 61/740,558, filed on Dec. 21, 2012.

(30) Foreign Application Priority Data

Dec. 21, 2012 (EP) .................................. 12198959

(51) Int. Cl.
*A01G 29/00* (2006.01)
*A01G 7/04* (2006.01)
(Continued)

(52) U.S. Cl.
CPC . *A01G 7/045* (2013.01); *G01J 3/28* (2013.01); *G01N 33/0098* (2013.01); *H05B 37/0227* (2013.01)

(58) Field of Classification Search
CPC ........ A01G 7/045; G01J 3/28; G01N 33/0098; H05B 37/0227
USPC ................................................ 47/17, 58.1 LS
See application file for complete search history.

(56) References Cited

U.S. PATENT DOCUMENTS

| 4,464,658 | A | 8/1984 | Thelen |
| 5,269,093 | A | 12/1993 | Horaguchi |

(Continued)

FOREIGN PATENT DOCUMENTS

| CN | 101965084 A | 2/2011 |
| CN | 201821534 U | 5/2011 |

(Continued)

OTHER PUBLICATIONS

Briggs, Winslow R. et al, "Phototropins 1 and 2: Versatile Plant Blue-Light Receptors" Trends in Plant Science, vol. 7, No. 5, May 2002, pp. 204-210.

(Continued)

*Primary Examiner* — Jason M Crawford

(57) ABSTRACT

The invention provides an interface (20) for converting a desired physiological plant response into control instructions for at least one lighting system (4,5) which has an adjustable lighting property, said interface (20) comprising: a receiver for receiving a desired physiological plant response; a processor functionally coupled to said receiver for converting said desired physiological plant response into said control instructions, and a transmitter (7), functionally coupled to said processor for transmitting said control instructions to said at least one lighting system (4,5) wherein said desired physiological plant response is defined as a set point in a multi-dimensional horticulture action space.

14 Claims, 12 Drawing Sheets

(51) Int. Cl.
*G01N 33/00* (2006.01)
*G01J 3/28* (2006.01)
*H05B 37/02* (2006.01)

(56) References Cited

U.S. PATENT DOCUMENTS

| | | | |
|---|---|---|---|
| 8,689,483 B2* | 4/2014 | Lin | A01K 1/02 47/17 |
| 2003/0005626 A1 | 1/2003 | Yoneda | |
| 2005/0252078 A1 | 11/2005 | Albright | |
| 2007/0289207 A1* | 12/2007 | May | A01G 7/00 47/17 |
| 2010/0020536 A1* | 1/2010 | Bafetti | F21V 23/003 362/231 |
| 2010/0031562 A1 | 2/2010 | Browne | |
| 2010/0076620 A1* | 3/2010 | Loebl | A01G 9/26 700/306 |
| 2011/0187291 A1* | 8/2011 | Plischke | H05B 37/02 315/312 |
| 2011/0215725 A1 | 9/2011 | Paolini | |
| 2012/0043907 A1 | 2/2012 | Lu | |
| 2013/0042527 A1* | 2/2013 | Aikala | H01L 33/06 47/58.1 LS |
| 2013/0294065 A1* | 11/2013 | Wells | F21V 29/02 362/231 |
| 2016/0000018 A1* | 1/2016 | Van Elmpt | F21K 9/56 47/17 |

FOREIGN PATENT DOCUMENTS

| | | |
|---|---|---|
| EP | 0241585 A2 | 10/1987 |
| WO | 2010053341 A1 | 5/2010 |

OTHER PUBLICATIONS

Sager, J.C. et al "Photosynthetic Efficiency and Phytochrome Photoequilibria Determination using Spectral Data", American Society of Agricultural Engineers, pp. 1882-1889.

Frechilla et al "Reversal of Blue Light-Stimulated Stomatal Opening by Green Light", Plant Cell Physiology, vol. 41, No. 2, 2000, pp. 171-176.

* cited by examiner

HORTICULTURE LIGHTING INTERFACE FOR INTERFACING AT LEAST ONE LIGHTING SYSTEM

CROSS-REFERENCE TO PRIOR APPLICATIONS

This application is the U.S. National Phase application under 35 U.S.C. §371 of International Application No. PCT/IB2013/061024, filed on Dec. 17, 2013, which claims the benefit of U.S. Provisional Patent Application No. 61/740,558, filed on Dec. 21, 2012 and European Patent Application No. 12198959.4, filed on Dec. 21, 2012. These applications are hereby incorporated by reference herein.

FIELD OF THE INVENTION

The invention relates to a horticulture lighting interface for interfacing at least one lighting system.

BACKGROUND OF THE INVENTION

Horticulture lighting is known in the art. US2010031562, for instance, describes a lighting installation for use in greenhouse farming for lighting crops in a greenhouse, comprising a number of light sources, such as lamps, provided above the crops to be lighted, and a number of dimmer devices for the light sources, characterized in that the dimmer devices are provided with control means for periodically, automatically varying the light intensity of the light sources cooperating with the dimmer devices according to a predetermined pattern. US2010031562 aims to provide a method and lighting installation, respectively, for greenhouse farming. In particular, the light sources are divided into a number of groups, the lighting installation being designed such that, in use, the power of each group varies according to a predetermined pattern, while patterns of different groups are phase-shifted relative to each other such that the electric power consumed by the joint groups varies less than the sum of the power variations of the separate groups, more particularly such that the electric power consumed by the joint groups varies less than the power variation of a single group, more particularly still such that the electric power consumed by the joint groups varies to a smallest possible extent, or does, at least virtually, not vary. In particular, all patterns are the same, but only phase-shifted relative to each other.

SUMMARY OF THE INVENTION

Plants use the process of photosynthesis to convert light, $CO_2$ and $H_2O$ into carbohydrates (sugars). These sugars are used to fuel metabolic processes. The excess of sugars is used for biomass formation. This biomass formation includes stem elongation, increase of leaf area, flowering, fruit formation, etc. The photoreceptor responsible for photosynthesis is chlorophyll and in higher plants also carotenoids as part of the antenna pigment. Apart from photosynthesis, also photoperiodism, phototropism and photomorphogenesis are representative physiological processes related to interaction between Light or electromagnetic radiation between 300 nm and 800 nm wavelength and plants:

photoperiodism refers to the ability that plants have to sense and measure the periodicity of Light (e.g. to induce flowering), phototropism refers to the growth movement of the plant towards and away from the Light, and photomorphogenesis refers to the change in form in response to the quality and quantity of Light.

Two important absorption peaks of chlorophyll a and b are located in the red and blue regions from 625-675 nm and from 425-475 nm, respectively. Additionally, there are also other localized peaks at near-UV (300-400 nm) and in the far-red region (700-800 nm). The main photosynthetic activity seems to take place within the wavelength range 400-700 nm. Radiation within this range is called photo synthetically active radiation (PAR).

The phytochrome photo system includes two forms of phytochromes, Pr and Pfr, which have their sensitivity peaks in the red at 660 nm and in the far-red at 730 nm, respectively. Phytochrome activity steers different responses such as leaf expansion, neighbor perception, shade avoidance, stem elongation, seed germination and flowering induction.

In horticulture, light often is quantified in nr of photons PAR (Photosynthetic Active Radiation) (the contribution to the photosynthesis of all photons between 400 and 700 nm is considered to be equal)) and can be measured and expressed in number of photons per second per unit of area (in $\mu mol/sec/m^2$; a mol corresponding to $6 \cdot 10^{23}$ photons). Alternatively, the light can be measured and expressed in terms of optical power (milli) watt.

Plant growth depends not only on the amount of light or light intensity, but also on spectral composition, duration, and timing of the light on the plant. The optimum light combination in terms of intensity, spectral composition, duration and timing and depending on the specific plant for plant development in term of these parameters is called a "light recipe".

Traditionally, only sunlight was available for plant growth. The development of artificial lighting and for instance greenhouses led to special lighting devices for that purposes. First light bulbs, lighting devices based upon heating wires, were used and high pressure sodium (HPS) lamps. HPS and Metal Halide lamps are both gas discharge lamps (the principle is bases on creating a discharge arc between 2 electrodes in a gas filled tube the arc ionizes the gasses and present metal halides or in case of HPS Sodium amalgam). Only incandescent bulbs (either vacuum or filled with halogen) are based on the principle of a heated wire mostly tungsten. A third principle often used is the fluorescent tube which is also a gas discharge lamp (filled with mercury vapor) the UV light created by the ionized mercury is converted by phosphors placed on the inside of the glass tube into visible light. All three lamp types are used for horticultural lighting. (HPS lamps often in greenhouses as assimilation lighting creating high light levels; Incandescent bulbs as flowering lamps (for blossom induction) also in green houses and fluorescent tubes in tissue culture growth and plant growth chambers without daylight. In principle the LED lighting can and eventual will replace the conventional light sources used for horticulture and probably will enable plant cultivation methods that are completely new and cannot be foreseen yet. With LEDs now it becomes possible to create any spectrum from 300 nm-800 nm more efficient then most conventional sources, but also controlling the spectral composition of a Led based light source is possible. LEDs can play a variety of roles in horticultural lighting, such as:

Supplemental lighting: Lighting that supplements the natural daylight is used in order to increase production (of tomatoes for example), extend crop production during e.g. the autumn, winter, and spring period when crop prices may be higher, or as a control method to tune morphology of the crop.

Photoperiodic lighting: The daily duration of light is important for many plants. The ratio of the light and dark period in a 24 hour cycle influences the blossoming response of many plants. Manipulating this ratio by means of supplemental lighting enables regulating the time of blossoming.

Cultivation without daylight in "plant factories" and for tissue culture applications.

In near future, conventional light source may continue to play a role. In some situations, they may prove to be more cost effective and/or proven artificial light source for plant growth. Possibly in combination with natural and/or other artificial light sources.

Various producers of lighting devices provided lighting devices having different characteristics, both in spectral output and/or in intensity. The light sources vary even more with the introduction of LED light sources. Furthermore, a grower may use and combine different types of lighting devices in his greenhouse. Combining all these different lighting devices in a greenhouse and providing the optimal type of lighting at the right stage of plant growth proves to be a challenge. In fact LED lighting makes the spectral composition controllable over time. Not only the quantity of the light is of concern but especially the quality of the light is of interest and needs to be defined.

Hence, it is an aspect of the invention to provide a lighting control for horticulture application and/or an alternative lighting method for horticulture application, which preferably further at least partly obviate one or more of above-described drawbacks.

The invention thus provides an interface for converting a desired physiological plant response into control instructions for at least one lighting system having at least adjustable lighting property, said interface comprising:

a receiver for receiving a desired physiological plant response;

a processor functionally coupled to said receiver for converting said desired physiological plant response into said control instructions, and a transmitter, functionally coupled to said processor for transmitting said control instructions to said at least one lighting system, wherein said desired physiological plant response is defined as a set point in a multi-dimensional horticulture action space, said multi-dimensional horticulture action space being represented by at least two dimensions selected from a first dimension representative for a desired photosynthesis action, a second dimension representative for a desired phototropine action, a third dimension representative for a desired phytochrome Pr action, and a fourth dimension representative for a desired phytochrome Pfr action, wherein said processor is functionally coupled to a memory comprising a description of a subspace of the multi-dimensional horticulture action space representing points in the multi-dimensional horticulture action space that are convertible into control instructions executable by said at least one lighting system, and wherein said processor is adapted for mapping said set point to a target point in said subspace and determine corresponding control instructions for said at least one lighting system.

In an embodiment, the invention provides an interface for converting a desired physiological plant response into control instructions for at least one lighting system having at least adjustable lighting property, said interface comprising:

a receiver for receiving a desired physiological plant response;

a processor functionally coupled to said receiver for converting said desired physiological plant response into said control instructions, and a transmitter, functionally coupled to said processor for transmitting said control instructions to said at least one lighting system.

Said desired physiological plant response is in an embodiment defined as a set point in a multi-dimensional horticulture action space, said multi-dimensional horticulture action space being represented by one of (i) a first coordinate system comprising at least a first dimension representative for a desired photosynthesis action and a second dimension representative for a desired phototropine action;

(ii) a second coordinate system comprising at least a first dimension representative for a desired photosynthesis action, a second dimension representative for a desired phytochrome Pr action and third dimension representative for a desired phytochrome Pfr action; and (iii) a third coordinate system comprising at least a first dimension representative for a desired phototropine action, a second dimension representative for a desired phytochrome Pr action and third dimension representative for a desired phytochrome Pfr action.

Said processor is functionally coupled to a memory comprising a description of a subspace of the multi-dimensional horticulture action space representing points in the multi-dimensional horticulture action space that are convertible into control instructions executable by said at least one lighting system, and said processor is adapted for mapping said set point to a target point in said subspace and determine corresponding control instructions for said at least one lighting system.

The horticulture action space coordinates can for instance be used in greenhouse control. In greenhouses, many different systems are present that support the growing of crop and other plants. In fact, in this respect, 'horticulture' may even extend to growing algae and comparable organisms.

The idea of combining fixed lighting devices with dimmable lighting devices sources and with full color controllable light sources in one lighting system and allowing easy spectrum control by using the horticulture action space is new and will be beneficial for both end-users installers, climate computer builders (programmers) and lamp manufacturers.

The horticulture action space can be used for more purposes:

1. To predict the response of plant to light and define light recipes for different crops.

2. To enable lamp manufactures to characterize the spectral composition of the lamps light that is relevant to plant growers.

3. Further use of the horticulture action space may be found in dynamic spectral control for growth light. Climate control systems can control the light spectrum of the light by communicating the correct coordinates without knowing the light spectrum of the lamps involved.

4. Light sensors measure the spectrum and can use the coordinates to define the spectral composition of both the artificial light and the ambient light.

Known systems that are present in greenhouses are feeding systems, relating to providing water and/with nutrients, ventilation systems that provide air with the right temperature and composition, for instance the right carbon dioxide content, and lighting system for providing the proper amount (intensity) and/or (spectral) composition of light at the right location. In some greenhouses, these systems are controlled by a climate control system.

In known greenhouse systems, growth recipes are provided that allows a grower to select the crop. The growth recipe then provides the climate control system with time-based data or may provide a time schedule, and settings for the feeding system and the ventilation system. In traditional greenhouses, the lighting systems may consist of a passive part and an active part. In this respect, the passive part may comprise shading means for changing the natural amount of light, often sunlight. The active part traditionally comprises artificial lighting devices like the HPS and Incandescent sources. In these traditional greenhouses, the climate control system may be able to actuate shading means and may be able to switch the artificial lighting devices on and off.

In modern lighting systems, more and more LED lighting devices which can have a combination of LED light sources are coming on the market. In general, LED light sources have a narrow and well-defined spectral output. In LED lighting devices, a plurality of LED light sources can be combined, and even different types of LED light sources in the sense of spectral output may be combined.

Light output may be defined as a combination of spectral output, the shape of the wavelength versus intensity curve, and intensity, the height of this curve. In some lighting devices, changing one of the spectral output and the intensity may influence the other.

Every lighting device may have different ways to control the light output. In a simple situation, like some LED-based lighting devices, LEDs can only be switched on or off. Thus, in such a lighting device, by switching on and off more or less of the LEDs, the intensity is controlled stepwise. In another light source, like a light bulb, by switching a light bulb on and off, the intensity is controlled in a binary way. By using for instance a dimming device, the light bulb light output is controlled in both the intensity as well as spectrally, but not independently.

In a greenhouse in the current situation, a grower in theory may thus be able to tune the lighting conditions in his greenhouse in every sense. In practice, however, in order to be able to control light conditions for affecting plant development, for instance software in a climate computer will need to have very detailed technical information on the installed lighting devices as well as their position in the greenhouse in order to control the spectral composition and intensity of the light and eventually the light received by the plants. Currently with conventional lighting, growers effectively cannot control the spectral composition of the light. Only the light level can be controlled. With LED lighting or a combination of LED lighting and conventional lighting the spectral composition may be controlled, for instance by the climate control computer. In order to accomplish this, detailed information on the installed lighting devices as well as their position in the greenhouse should be available to the climate computer in order to create the correct light levels and spectral composition of the light at the plant level. Also, the results of research institutes providing optimal lighting conditions need to be translated into settings that are within the capabilities of the available lighting system.

A current development is to produce light recipes that can be used in for instance climate computers and light control devices for lighting devices. Apart from light control devices also light sensors can be used to measure one or more of the ambient light level (intensity and/or spectral composition) and light levels of artificial lighting devices in a greenhouse.

The communication between all these components is complex and now depends on individual devices.

The development of the horticulture action space allows the controls to become less dependent on the technical construction of the lighting devices and the other components. Another advantage is that with definition of the horticulture action space, only the correct coordinates need to be calculated and generated. The same coordinates may be generated by different lighting devices and using different spectra. Now the most efficient way to generate a required and/or desired lighting condition can be used. This may be either on energy efficiency, on cost efficiency, and even based upon ergonomic requirements. In some situations, a human should be able to judge the status of crop or plants. The effect on the plant, however, would be the same.

The horticulture action space can be used to predict the response of plant to light and define light recipes for different crops. The horticulture action space on the other hand may enable lamp manufacturers to characterize the spectral composition of the output of lighting devices in a way that is relevant and understandable to plant growers. It may also provide a clear and transparent way to communicate the effect of the lamp or the quality of the lamp to growers. Further use of the horticulture action space may be found in dynamic spectral control for growth light. Climate control systems may be able to control the light spectrum of lighting devices by communicating the correct coordinates without detailed knowledge of the exact light spectrum of the lamps involved. Light sensors may measure the resulting spectrum and may be able to communicate the results in the form of coordinates in the horticulture action space.

Thus, only the coordinate control area of a plants light recipe needs to be implemented in the control software and can be used as long as the lamps can be operated within the desired color area. Lamp dependent reprogramming is simplified. The architecture of the lamp driver may not be relevant to the control software anymore. The light recipe does not need to be build into the lighting device, but can be sold to the end-user as a software add-in for the climate control software. Alternatively, light recipes can be provided in a remote database that can be accessed for instance by the interface.

A feature of the horticulture action space is that the spectral composition of light that is offered to a plant can be expressed in plant relevant unities. These unities are derived from plants absorption and response/action characteristics. The spectral composition of light is translated in the horticulture action space into a point or coordinate in the horticulture action space. This point is further communicated and translated into light intensity and spectral composition towards the installed lighting systems. Thus, it may simplify communication between growers, plant physiologists, biologists, developers of greenhouses and greenhouse climate control systems, and lamp manufactures.

In plant physiology studies, it was found that several parts in the light spectrum are responsible for various aspects in plant development. Over the years, this led to the definition of several so called action spectra. These action spectra represent the relative contribution of a spectral component and its relative effect on the development of plants. In other words, it defines the relative effectiveness of different wavelengths of light to induce a biological response. These action spectra also relate to the presence of photosensitive components in plants, like chlorophyll.

One of the action spectra that are well defined in literature is the McCree action spectrum. This action spectrum allows relating the amount of photosynthesis in an average plant to light conditions. It is based upon the photosynthetic activity of an average plant. Its validity is for instance recently confirmed in E. Paradiso et al., Spectral dependence of photosynthesis and light absorptance in single leaves and canopy in rose, Science Horticulturae 127 (2011), pp. 548-554. The McCree curve was first identified by McCree in 1972, and was validated is this publication.

In other studies, the effect called phototropism is identified. This effect is induced by so called phototropins, blue-light receptors in plants, which induce besides phototropism for instance chloroplast migration and blue-light-induced stomatal opening. It is responsible for instance for the growth movement of plants towards and way from light. This is for instance described in Winslow R. Briggs and John M. Christie, Phototropins 1 and 2: versatile plant blue-light receptors, Trends in Plant Science Vol. 7 No 5, May 2002, pp 204-210.

In other studies, two interconvertable forms of phytochromes were identified. They are also referred to as Pr and Pfr action spectra. The importance of phytochromes can be evaluated by the different physiological responses where they are involved, such as leaf expansion, neighbor perception, shade avoidance, stem elongation, seed germination and flowering induction. The two important action spectra in this respect are a Far-red absorbing form of phytochromes (Pfr), and a Red absorbing form of phytochromes (Pr). The relevant action spectra and calculation of phytochrome photoequilibria are for instance identified in J. C. Sager et al., Photosynthetic Efficiency and Phytochrome Photoequilibria Determination Using Spectral Data, American Society of Agricultural Engineers 0001-2351/88/3106, pp 1882-1889.

These above-explained and discussed action spectra have been combined into the horticulture action space that is used in the current document. For most green plants, these action spectra can be used. For other plants, including algae, other action spectra may be required. These specific action spectra can be used in the same way as the action spectra identified above.

It was found that using the two dimensions, already allows a description of lighting conditions which may be used in cases where a limited amount of and/or type of lighting devices are used. It was found that in that case, these two coordinates give the best description. It may be needed, however, to use a more detailed horticulture action space definition.

The horticulture action coordinates in an embodiment represent at least an amount of photosynthesis action and an amount of phototropine action. A definition to calculate such an amount is to incorporate all contributions to the specific action for all relevant wavelengths of light, taking into account the weighted contribution. In this respect, the proper weight depends on the intensity of the light at a certain wavelength that is considered. A way of calculating the amount of action is by taking for each relevant wavelength the relative amount of action, and summing those relative amounts for all relevant wavelengths.

It is evident that there are thus different ways of calculating a horticulture action space that can be used in horticulture applications.

In the current invention, several steps were taken in order to come to a horticulture action space that allows communication regarding lighting conditions and that is as much as possible independent of exact spectral properties of lighting devices that are present in a greenhouse. An advantage of the definition below is that allows a definition that is clear, it provides a space that is as linear as possible, and it allows calculation of various other quantities that can be used in plant-biological processes.

Below, an example of a horticulture action space based upon the principles explained above is elucidated in detail. Other useful horticulture action spaces may be possible. It was found, however, that the definition below provides a space that is as linear as possible, provides insight in all involved parties, and is relatively easy to understand and use in practice. This horticulture action space can be used for most known green plants.

A four-dimensional horticulture action space can be defined as follows. First, the following values are defined:

$$W = \int_{300nm}^{800nm} I(\lambda) \cdot Pfr(\lambda) d\lambda$$

$$X = \int_{300nm}^{800nm} I(\lambda) \cdot Pr(\lambda) d\lambda$$

$$Y = \int_{300nm}^{800nm} I(\lambda) \cdot Photosynthesis(\lambda) d\lambda$$

$$Z = \int_{300nm}^{800nm} I(\lambda) \cdot Photropine(\lambda) d\lambda$$

In these equations, $I(\lambda)$ is defined as the radiant flux in Watt. In order to use these values, the action spectra explained above are normalized. In FIG. 5, which will be explained in more detail below, the normalized action spectra are plotted. Each action spectrum is in fact normalized such that its maximum value is 1. For the $Pfr(\lambda)$ action spectrum, the normalization of the $Pr(\lambda)$ action spectrum is used as these action spectra in practice are interrelated. The values W, X, Y, Z are then normalized into a 4-dimensional normalized space:

$$w = \frac{W}{W+X+Y+Z}$$

$$x = \frac{X}{W+X+Y+Z}$$

$$y = \frac{Y}{W+X+Y+Z}$$

$$z = \frac{Z}{W+X+Y+Z}$$

An advantage of this definition of the horticulture action space is that calculations are simplified, communication of the plant action becomes meaningful as the space becomes normalized. These normalized coordinates, however, also require that an indication of absolute light intensity is also communicated. A most simple way is communicating the integral of $I(\lambda)$ over the relevant wavelengths, "I", together with the coordinates. A more elegant way is communicating one of the horticulture action space coordinates in its absolute value. In the communication of horticulture action space coordinates, the Y value is an absolute measure of the amount of photosynthesis. In an embodiment, the Y is therefore communicated as one of the coordinates. In an embodiment, Y is used together with x. Alternatively, Y is used together with x and y.

In an alternative embodiment, (z, x, w) or (x, y, w) are used as a minimum set. Again, one of these coordinates can be used in its absolute value ("capital"), or if not present, Y can be added.

A way to pinpoint the exact horticulture action coordinate is using the (W,X,Y,Z) coordinate. In order to more easily to compare light sources quality of light, (x,y,z) is relevant, and note that w=1-x-y-z. A complete coordinate set can be (x,y,z,Y), because from this set (or space) the (W,X,Y,Z) coordinate can be calculated:

$$W = w*(W+X+Y+Z) = w*(Y/y)$$

$$X = x*(Y/y)$$

$$Z = z*(Y/y)$$

In particular, in a 4-dimensional space the quality of light can be expressed in the 3-D (x,y,z) coordinate and the quantity of light in the Y value. Again, this set (x, y, z) needs to have an indication of light intensity in order to make calculations regarding light systems. Again, 'I' can be added, Y can be added or used instead of y, or one or more of the other coordinates may be used in its absolute ("capital") form.

From the horticulture action space coordinates, various quantities can be calculated that relate directly to plant action. In these calculation, the already-mentioned total light intensity 'I', defined as radiant flux (again, in watt) is used:

$$I = \int_{300\ nm}^{800\ nm} I(\lambda)d\lambda$$

$$PSS = \frac{X}{W+X}$$

Relative photosynthetic activity = $Y/I$

Relative phototropine response = $Z/I$

In this respect, PSS is also defines as Pr/(Pr+Pfr). In communicating and defining the horticulture action space, as explained the total amount of optical energy was found to be an important parameter. The explanation above shows that instead of communicating 'I', it provides more insight into the nature of the coordinates if 'Y' is used.

In the current calculations, the coordinates are calculated using an optical wavelength range of 300-800 nm. It may be possible to expand that range to a broader wavelength range if needed. For instance, there may be plants or algae that show activity in other ore broader wavelength ranges.

In an embodiment, the processor is adapted to project or map said set point in said subspace based on at least one optimizing criterion. Such an optimization criterion may for instance be the amount of energy used by the lighting system or the complete lighting system of a greenhouse, for instance. Alternatively, a grower may have preferences regarding the use of certain lighting systems or light sources in the lighting system.

In an embodiment, the multi-dimensional horticulture action space comprises at least a first dimension representative for a desired photosynthesis action, a second dimension representative for a desired phototropine action, a third dimension representative for a desired phytochrome Pr action, and a fourth dimension representative for a desired phytochrome Pfr action.

These four dimensions together were found to be able to predict plant development for a large part. The exact calculations for these dimensions are already explained above.

In an embodiment, the multi-dimensional horticulture action space comprises a further dimension, said further dimension representative for a desired stomata opening action. The stomata opening and possible action spectrum is described for instance in Silvia Frechilla et al., "Reversal of Blue Light-Stimulated Stomatal Opening by Green Light", Plant Cell Physiol. 41(2): 171-176 (2000). This further dimension can be defined similar as the other dimensions explained above.

In an embodiment, the receiver is further adapted to receive a horticulture light recipe comprising at least a label for identifying a type of plant, at least one desired physiological plant response, and a time schedule for said at least one desired physiological plant response, with said at least one desired physiological plant response represented as at least one horticulture action coordinate. The horticulture light recipe can thus comprise a time schedule with a series of horticulture action coordinates corresponding with the time schedule. Thus, the development of the plant can be controlled and directed. Multiple light recipes can be provided in a database that can be remote from the interface. It may be accessed by the interface via a network, for instance via the internet.

In an embodiment, said receiver is further adapted for receiving a lighting system definition comprising a lighting system identification with associated control instructions for executing physiological plant responses defined as points defining said sub space in said multi-dimensional horticulture action space, and which control instructions are executable by said at least one lighting system, and said receiver is adapted for providing said lighting system definition to said memory. In an embodiment, multiple lighting system definitions can be provided in a lighting database. Again, that lighting database can be remote from the interface. It may be accessed by the interface via a network, for instance via the internet. Such a set of lighting system definitions allows swift switching between lighting systems. It allows combining various lighting systems. These lighting systems may be complementary or supplementary. It can allow a fast selection of lighting systems that need to be used in order to have a defined plant development.

In an embodiment, the receiver is further adapted for receiving a sensor value representative for a sensed light spectrum, and wherein the processor is further adapted for mapping said sensor value to a sensed point in said multi-dimensional horticulture action space. In this way, it is possible to integrate actual lighting conditions. This may provide, for instance feedback for controlling the at least one lighting system.

In an embodiment, the interface further comprising a display, functionally coupled to said processor, for displaying the sub space of said at least one light system relative to the horticulture action space, or for displaying projections thereof, preferably the display additionally displays at least one of said set point and said target point relative to said sub space, of projections thereof. Such a display may for instance provide feedback to a user, for instance a grower in a greenhouse. The display may for instance be integrated in a hand-held device and thus provide feedback to a grower during his work in for instance a greenhouse. When for instance combining the display with the previously mentioned sensor values and allowing the display to also include said sensed point, a grower may compare the desired settings and resulting effect visually and on the spot. The display can be a visual computer screen, for instance an LCD or OLED screen. It may be provided with a so called touch interface.

The invention further pertains to a horticulture system, comprising a horticulture lighting interface described above, at least one lighting system, and a climate control system. In this horticulture system, the interface is functionally coupled with a climate control system for providing at least one desired physiological plant response to said interface and further functionally coupled with a lighting system for receiving control instructions from said interface and to provide light mapped to said at least one desired physiological plant response. The interface may be physically separated from, and even be remote from, the at least one of the climate control system and the at least one lighting system. In such embodiments, transfer of data may be realized in a known way, for instance wireless. In such an embodiment, the interface may be a separate unit, even provided in a separate housing. Alternatively, the interface may be incorporated into at least one of the climate control system and the lighting system. In such an embodiment, the interface may even be a software element or add-on that runs in either the climate control system and is thus added to or incorporated into software running on the climate control system. It may also be running in the lighting system and/or may be integrated in software running on the lighting system.

The invention further pertains to a horticulture system, comprising the horticulture lighting interface described above, and a horticulture light recipe management system. The horticulture light management system is adapted to provide a horticulture light recipe comprising at least a label for identifying a type of plant, at least one desired physiological plant response defined as at least one set point in said multi-dimensional horticulture action space, a time schedule for said at least one desired physiological plant response, wherein said interface is functionally coupled to said horticulture light recipe management system for receiving said horticulture light recipe. The light recipe management system may be remote from the interface and even be remote from for instance the physical location of a greenhouse using the horticulture system. It may be accessible via a network, for instance via the internet. The interface and the light recipe management system may exchange information, like one or more light recipes, and the interface subsequently provides resulting lighting system control instructions to one or more lighting systems.

The invention further pertains to a horticulture system comprising the horticulture lighting interface described above, further comprising a lighting management system comprising a repository of lighting system definitions each comprising a lighting system identification with associated control instructions for executing physiological plant responses defined as points defining said sub space in said multi-dimensional horticulture action space, and wherein said interface is functionally coupled to said lighting management system for accessing said repository. The interface and the lighting management system may be remote from one another. The lighting management system may even be remote from for instance a greenhouse using the horticulture system. The lighting management system may be coupled to the interface via a network, for instance via the internet. The interface and the lighting management system may exchange information, like one or more lighting system definitions, and the interface subsequently provides resulting lighting system control instructions to one or more lighting systems. It may for instance select one or more of the available lighting systems that may be installed in a greenhouse and that need to be used.

The invention further pertains to a sensor for providing a sensor value representative for a sensed light spectrum, wherein said sensor is functionally coupled to a sensor interface for converting said sensor value into an estimated physiological plant response, said sensor interface comprising:

a receiver for receiving a sensor value;

a processor functionally coupled to said receiver for converting said sensor value into said estimated physiological plant response, and a transmitter, functionally coupled to said processor for transmitting said estimated physiological plant response.

Said estimated physiological plant response is defined as an estimation point in a multi-dimensional horticulture action space, said multi-dimensional horticulture action space being represented by one of (i) a first coordinate system comprising at least a first dimension representative for a desired photosynthesis action and a second dimension representative for a desired phototropine action;

(ii) a second coordinate system comprising at least a first dimension representative for a desired photosynthesis action, a second dimension representative for a desired phytochrome Pr action and third dimension representative for a desired phytochrome Pfr action; and (iii) a third coordinate system comprising at least a first dimension representative for a desired phototropine action, a second dimension representative for a desired phytochrome Pr action and third dimension representative for a desired phytochrome Pfr action.

Said processor is adapted for mapping said sensor value to said estimation point. The sensor is easily integrated in a horticulture system using the horticulture action space. In an embodiment, the sensor values are spectral measurement data. In such an embodiment, spectral data can be provided at regular wavelength intervals. For instance, values can be provided every 10 nm, or every 20 nm. In the embodiment for horticulture applications, sensor values may be provided for a wavelength interval of 300-800 nm. The sensor may be provided with a dispersive element and a spatial detector, for instance a CCD strip detector or a 2D CCD sensor. Alternatively, a sensor may be provided with a series of filters en one or more detectors. This, in fact, is known to a skilled person. The sensor values in fact may directly provide the $I(\lambda)$ values that are used for calculating X, Y, Z, W as explained above, or it may provide sensor values from which $I(\lambda)$ can be derived.

The invention further pertains to a method for converting a desired physiological plant response into control instructions for at least one lighting system having at least one adjustable lighting property, said method comprising:

receiving a desired physiological plant response, wherein said desired physiological plant response is defined as a set point in a multi-dimensional horticulture action space, said multi-dimensional horticulture action space being represented by one of (i) a first coordinate system comprising at least a first dimension representative for a desired photosynthesis action and a second dimension representative for a desired phototropine action;

(ii) a second coordinate system comprising at least a first dimension representative for a desired photosynthesis action, a second dimension representative for a desired phytochrome Pr action and third dimension representative for a desired phytochrome Pfr action; and (iii) a third coordinate system comprising at least a first dimension representative for a desired phototropine action, a second dimension representative for a desired phytochrome Pr action and third dimension representative for a desired phytochrome Pfr action;

converting said desired physiological plant response into control instructions, the converting comprising mapping said set point to a target point in a subspace of the multi-dimensional horticulture action space and determining corresponding control instructions for said at least one lighting system, wherein said subspace comprises points in the multi-dimensional horticulture action space that are convertible into control instructions for said at least one lighting system and executable by said at least one lighting system; and transmitting said control instructions to said at least one lighting system.

In the current description, the lighting systems comprise lighting devices that can be adaptable in intensity, in emission spectrum, or both. Currently, for instance LED-based lighting devices are marketed.

The LEDs can be solid state LEDs, but may optionally also be organic LEDs. Also combinations of solid state and organic LEDs may be applied. In fact, the current application provides a solution for any type of lighting device. The term "LED" may also relate to a plurality of LEDs. Hence, in an embodiment, at a single LED position, a plurality of LEDs may be arranged, such as a LED package of 2 or more LEDs. The LEDs are especially designed to generate (LED) light in the first wavelength range.

The advent of solid state lighting based on LEDs offers opportunities for application in horticulture. The main advantages of using LEDs result from the possibility to control the spectral composition of the light to closely match the plant's photoreceptors. Together with additional benefits like improved heat control and freedom of distributing the LEDs, this provides a more optimal production and enables influencing the plant's morphology and composition. It also promises a reduced energy consumption (and associated cost).

Because they are solid-state devices, solid state LEDs are easily integrated into digital control systems, facilitating lighting programs such as "daily light integral" lighting and sunrise and sunset simulations. LEDs are safer to operate than current lamps because they do not have glass envelopes and do not contain mercury.

LEDs enable one to distribute the light closer to the target which can result in less loss through the roof and the floor of the greenhouse. Moreover a better light distribution in the crop can be accomplished. This is certainly the case for high-wire crops like tomatoes.

In the interface, the receiver and transmitter may be software implemented, or they may be hardware implemented. The processor may be a general purpose microprocessor running machine instructions. The memory can en any type of memory, for instance digital memory that can be functionally coupled to the general purpose microprocessor. Known memory means are RAM, ROM, flash memory, hard disks, and the like. These types of memory can be physically connected to the interface and in fact to the processor. Alternatively, the memory is wireless connected, it may even be remote from the processor, and accessible via a network or the internet, for instance.

The control instructions for the lighting system may be simple on/off instructions. In more advanced lighting systems, they may be instructions setting an output level, for instance 0%, 50%, 100%. These settings may even be continuous, between 0 and 100 for instance. In even more advanced systems, using for instance different types of LED sources, the control instructions may define which sources are to be switched on and off, and even the power output of each source may be defined. In even more advanced source, the spectral output may even be defined.

In the interface, the subspace of the multi-dimensional horticulture action space is a description of points that may be feasible using the at least one lighting system. In the mapping, the set point may be simply a point in the subspace. And even then, it may be worthwhile to not provide the control instructions that actually generate that exact set point, but to find a related target point that is within a defined range of the set point but which fulfills criteria like for instance energy consumption of the lighting system under these control instructions, or other criteria, like additional heat production, use of certain available light sources, in particular an optimal use of natural light sources.

In case the set point is outside the subspace, an approximation may be calculated. This may be done in various way, and using various optimization criteria. For instance, a closest point in the subspace that is closest to the set point may be selected first. Subsequently, the optimization illustrated above may be done.

The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

As indicated above, the invention also provides a method of providing growth light in horticulture applications comprising providing at least part of the crop with horticulture light from the lighting device according to any one of the preceding claims. Especially, the method may comprise varying the spectral intensity distribution of the horticulture light as a function of one or more of (a) the addressed part of the plant or crop, (b) the time of the day, (c) the light intensity and light distribution of other light than the Artificial light, (d) the type of Crop or plant cultivar (e) the growth stage of the Plant or crop, (f) the stage of a horticulture crop, (g) the time to harvest, (h) the time from harvest, and (i) position in horticulture arrangement.

Horticulture relates to (intensive) plant cultivation for human use. When illuminating horticulture, the term "horticulture" may relate to production cultivation of plants for food (fruits, vegetables, mushrooms, culinary herbs) and non-food crops (flowers, trees and shrubs, turf-grass, hops, grapes, medicinal herbs or crops for feed). The term horticulture may especially refer to food crops (tomatoes, peppers, cucumbers and lettuce), as well as to plants (potentially) bearing such crops, such as a tomato plant, a pepper plant, a cucumber plant, etc. Horticulture may herein in general relate to e.g. crop and non-crop plants. Examples of crop plants are Rice, Wheat, Barley, Oats, Chickpea, Pea, Cowpea, Lentil, Green gram, Black gram, Soybean, Common bean, Moth bean, Linseed, Sesame, Khesari, Sunhemp, Chillies, Brinjal, Tomato, cucumber, Okra, Peanut, Potato, Corn, Pearlmillet, Rye, Alfalfa, Radish, Cabbage, lettuce, pepper, Sunflower, Sugarbeet, Castor, Red clover, White clover, Safflower, Spinach, Onion, Garlic, Turnip, Squash, Muskmelon, Watermelon, Cucumber, Pumpkin, Kenaf, Oilpalm, Carrot, Coconut, Papaya, Sugarcane, Coffee, Cocoa, Tea, Apple, Pears, Peaches, Cherries, grapes, Almond, Strawberries, Pine apple, Banana, Cashew, Irish, Cassava, Taro, Rubber, Sorghum, Cotton, Triticale, Pigeonpea, and Tobacco. Especial of interest are tomato, cucumber, pepper, lettuce, water melon, papaya, apple, pear, peach, cherry, grape, and strawberry.

Horticulture may take place in a greenhouse. The interface may be used especially relates to the application of the interface and/or the method in a greenhouse. When used in or with lighting systems, these lighting systems may be arranged at different places in a growing system. For instance, the lighting system may be arranged between crop, or between crop-to-be, which arrangement is indicated as "inter lighting". Horticulture growth on wires, like tomato plants, may be a specific field of inter lighting that may be addressed with a lighting system. The lighting system may also be arranged over crop or crop-to-be. Especially when horticulture is grown in layers over each other, artificial lighting is necessary. Growing horticulture in layers is indicated as "multi-layer growth". Also in multi-layer growth, the interface and/or method may be applied.

The invention provides a new way of controlling artificial lighting used to stimulate plant growth and development, a technique that is known as horticultural lighting. In particular, there are two major horticultural environments in which artificial lighting is used. Firstly, greenhouses increase crop yields using top lighting and intracanopy lighting in addition to daylight. Secondly, in multilayer systems the crops grow mainly without daylight and, thus, depend heavily on artificial lighting. Also, the invention relates to photoperiodic lighting, for instance for controlling flowering.

The term "substantially" used in this application, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 11 shows the interface implemented in a climate computer in a greenhouse, FIG. 12 shows the interface separate from the climate computer, FIG. 13 shows the interface implemented in a lighting control device, FIG. 14 shows the interface implemented in a sensor, and FIG. 15 shows an embodiment of a basic configuration of an interface with a lighting system interface part.

The drawings are not necessarily on scale.

DETAILED DESCRIPTION OF THE EMBODIMENTS

Figure 1:
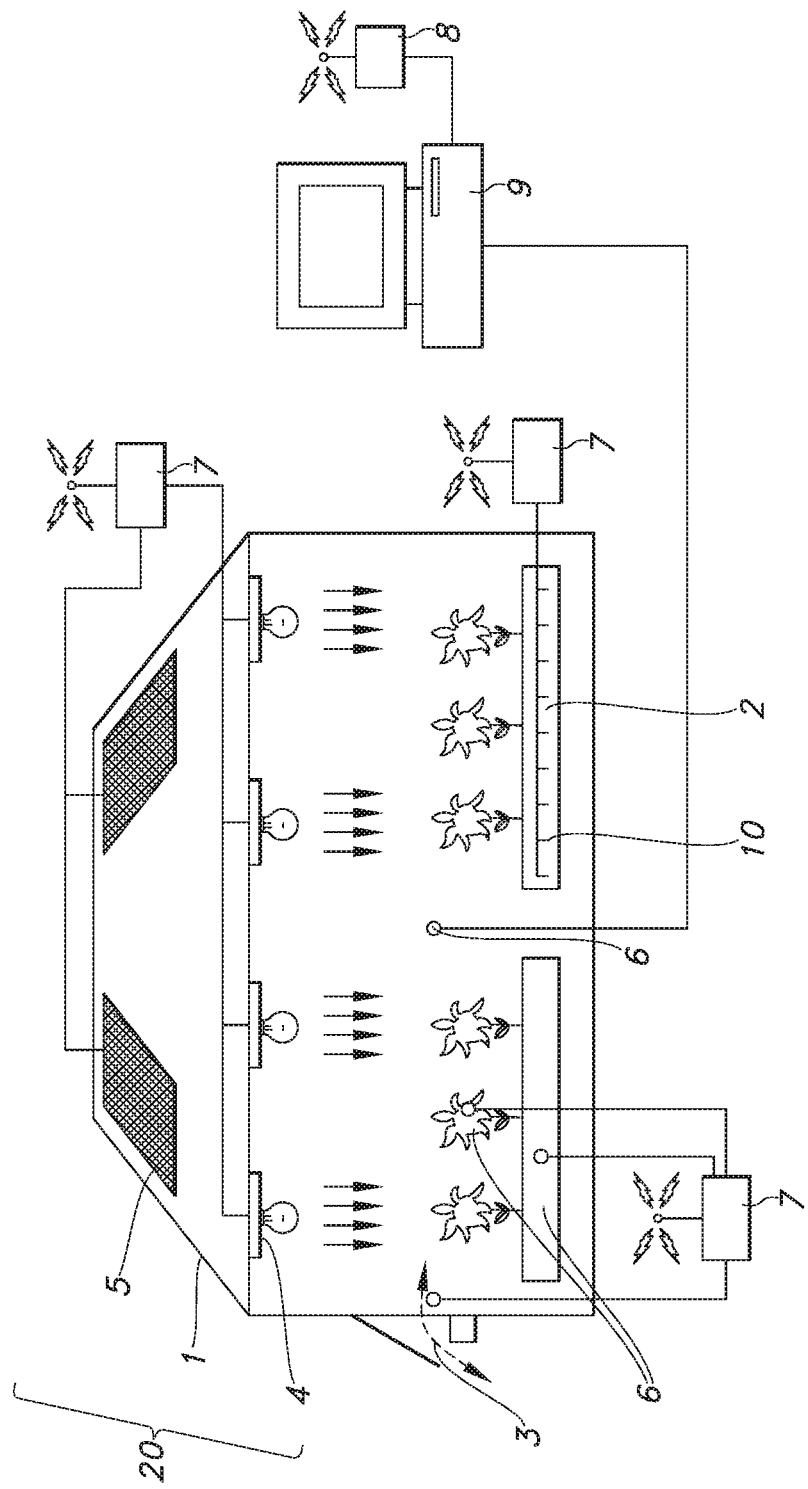
FIG. 1 schematically depicts an example of a greenhouse comprising a climate control system and including a lighting system.

FIG. 1 shows schematically an example of a greenhouse 1 with various systems. Such a greenhouse 1 is for instance described in U.S. Pat. No. 8,061,080 of the current applicant. It shows a state of the art greenhouse 1. Such a greenhouse 1 comprises a climate system. In this embodiment, the climate system comprises a feeding system 2 for providing water and nutrients, an ventilation system 3 for providing air having the right composition (carbon dioxide content, for instance), and at the right temperature. Furthermore, the climate system of this greenhouse comprises a lighting system 4,5. In the embodiment of FIG. 1, the components of the climate system, i.e. the feeding system 2, ventilation system 3 and lighting system 4, 5, are wirelessly coupled via transmitters 7 to transmitter 8 of a climate control system 9. In this embodiment, the greenhouse further comprises sensors 6, for instance for determining lighting conditions, temperature, humidity. These sensors are also wirelessly coupled via transmitters 7 to the climate control system 9. In this greenhouse, plants 11 are situated in a substrate 10.

In the embodiment of FIG. 1, the lighting system 4, 5 comprises an active lighting system 4 comprising for instance lighting devices like traditional incandescent lighting devices, but may also comprise LED lighting devices. The lighting system 4, 5 further comprises in this embodiment a passive lighting devices 5, here shading means for reducing the amount of incoming sunlight.

Figure 2:
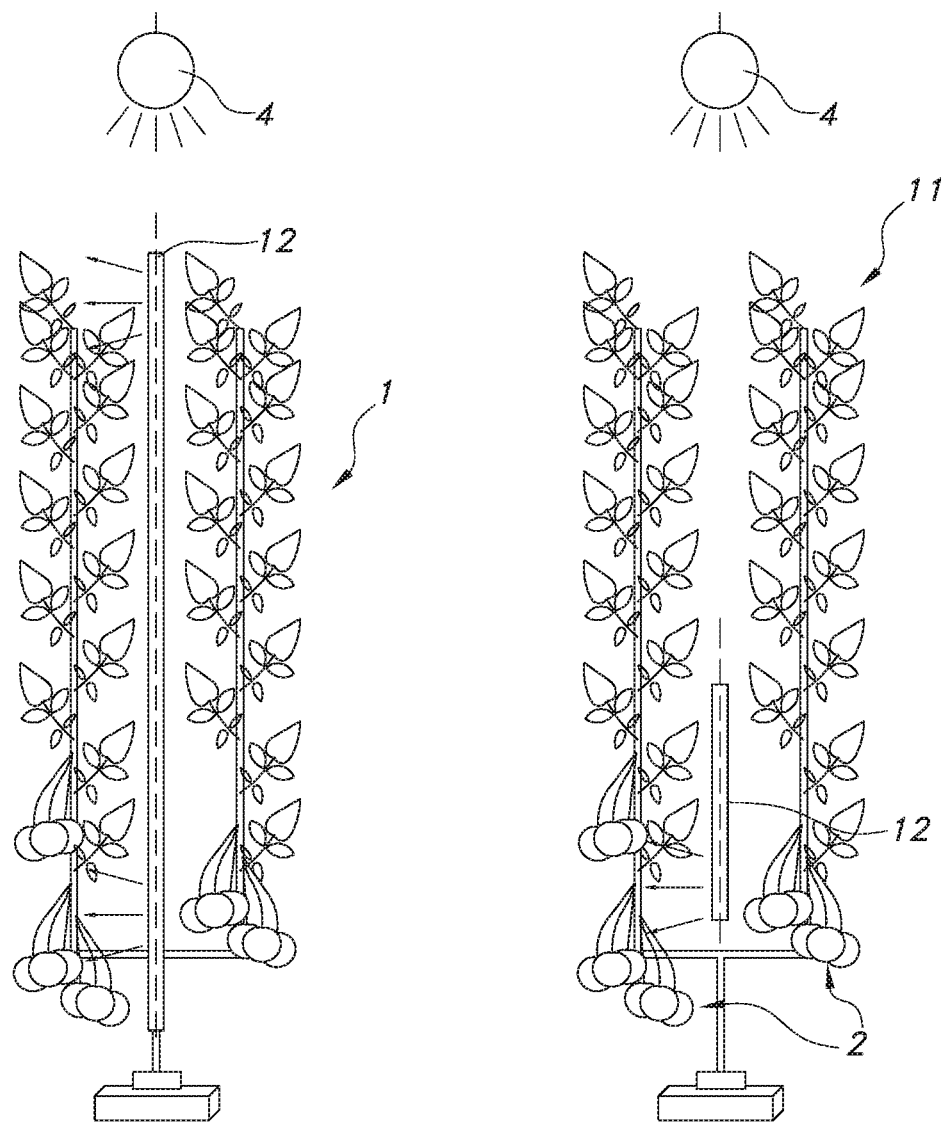
FIG. 2 schematically depicts a setting of plants in a greenhouse with different types of lighting devices.

FIG. 2 schematically shows an example of plants 11 in a greenhouse with different types of lighting devices 4, 12 that may be present. As such, these lighting devices are known to a skilled person. First, the greenhouse may be equipped with one or more traditional lighting devices 4. These traditional lighting devices may comprise a incandescent-based lighting device 4. This type of lighting device can originate from various manufacturers. Depending on the manufacturer, even the same type of lighting device can vary in emission spectrum. Furthermore, a lighting device ages, which may also change its emission spectrum.

Furthermore, localized lighting devices 12 like a LED lighting devices 12 can be present in a greenhouse, varying from lighting devices that provided local lighting, and lighting devices that provide general lighting. With LED lighting devices 12, the emission spectra can vary and/or total light intensity can be varied even more than with traditional lighting devices.

Furthermore, the lighting system may comprise one or more shading devices 5, indicated in FIG. 1. This may also be regarded as a control device for a particular lighting device, namely a natural lighting device, the sun.

Combining all these lighting devices (and, in fact, including the shading device) each with their own emission spectrum and intensity make it complex for a grower to provide the right light conditions to his crop at the right time.

In the current invention, several steps were taken in order to come to a horticulture action space that allows communication regarding lighting conditions and that is as much as possible independent of exact spectral properties of lighting devices that are present in a greenhouse.

As already explained, the four-dimensional space can be defined as follows. First, the following values are defined:

$$W = \int_{300nm}^{800nm} I(\lambda) \cdot Pfr(\lambda) d\lambda$$

$$X = \int_{300nm}^{800nm} I(\lambda) \cdot Pr(\lambda) d\lambda$$

$$Y = \int_{300nm}^{800nm} I(\lambda) \cdot \text{Photosynthesis}(\lambda) d\lambda$$

$$Z = \int_{300nm}^{800nm} I(\lambda) \cdot \text{Photropine}(\lambda) d\lambda$$

Figure 3:
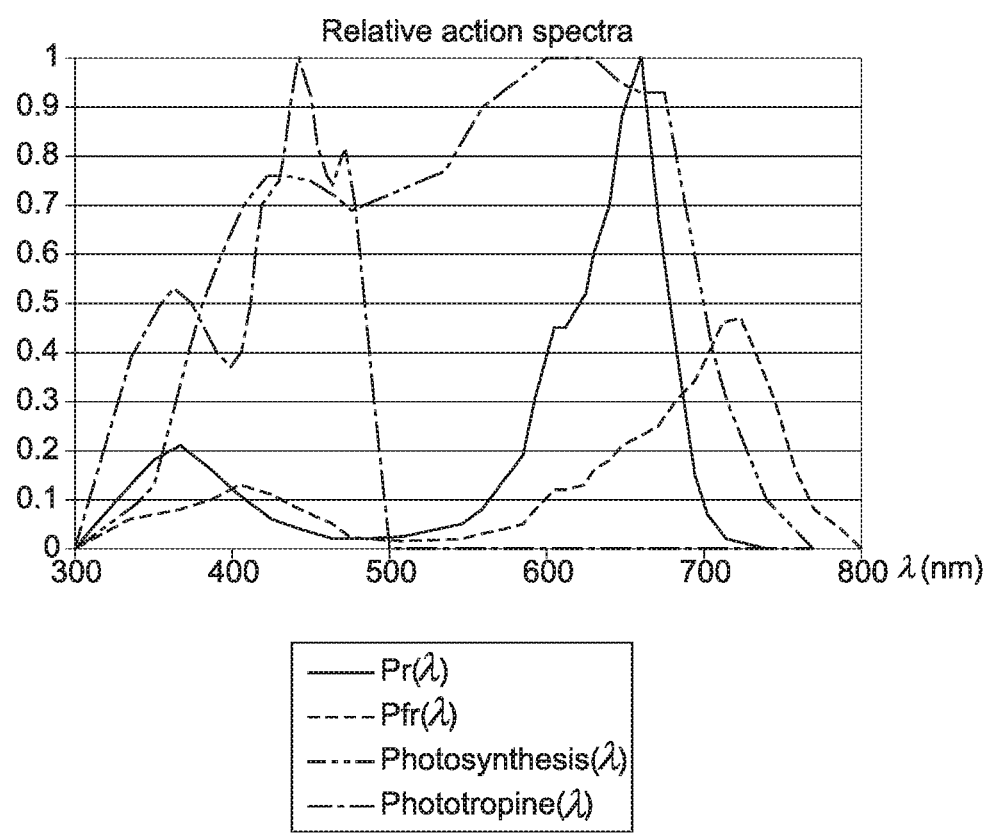
FIG. 3 depicts fundamental plant action spectra that can be used in calculation of the horticulture action space.

In order to use these values, the action spectra explained above are first normalized. In FIG. 3, the normalized action spectra are plotted. Each action spectrum is in fact normalized such that its maximum value is 1. For the Pfr(λ) action spectrum, the normalization of the Pr(λ) action spectrum is used as these action spectra in practice are interrelated. The values W, X, Y, Z are then normalized into a 4-dimensional normalized space:

$$w = \frac{W}{W+X+Y+Z}$$

$$x = \frac{X}{W+X+Y+Z}$$

$$y = \frac{Y}{W+X+Y+Z}$$

$$z = \frac{Z}{W+X+Y+Z}$$

In the communication of horticulture action space coordinates, the Y value is communicates together with x, y as a minimum set, or (w, x, y, z and Y) as a complete set. From the horticulture action space coordinates, various quantities can be calculated that relate directly to plant action. In these calculation, the total light intensity is used:

$$I = \int_{300\,nm}^{800\,nm} I(\lambda) d\lambda$$

$$PSS = \frac{X}{W+X}$$

Relative photosynthetic activity = $Y/I$

Relative phototropine response = $Z/I$

Figure 4:
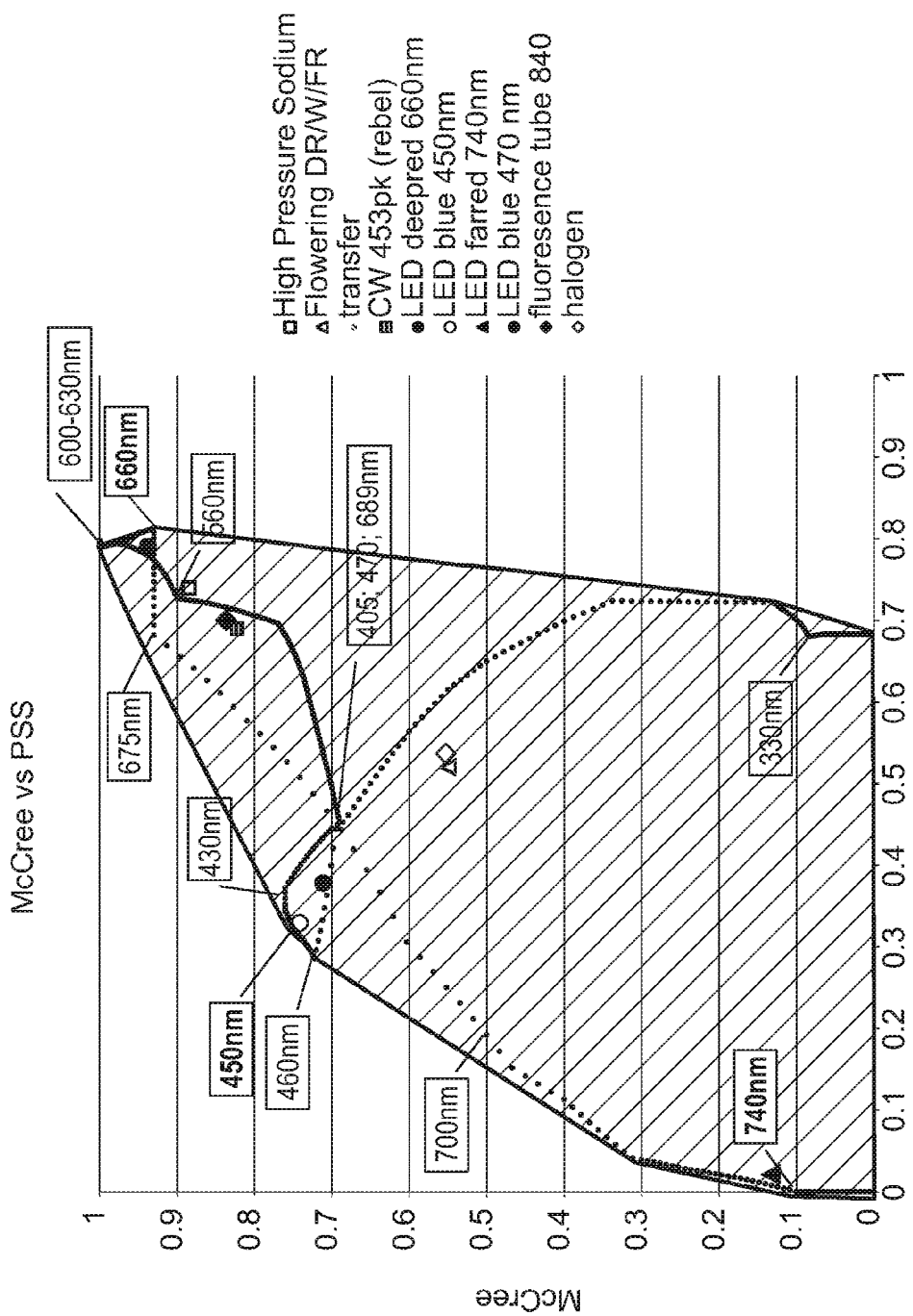
FIGS. 4-6 show projections of the horticulture action space showing respectively McCree versus PSS, Phototripine versus PSS and Phototripine versus McCree, and the positions of various lighting devices in the horticulture action space.
Figure 5:
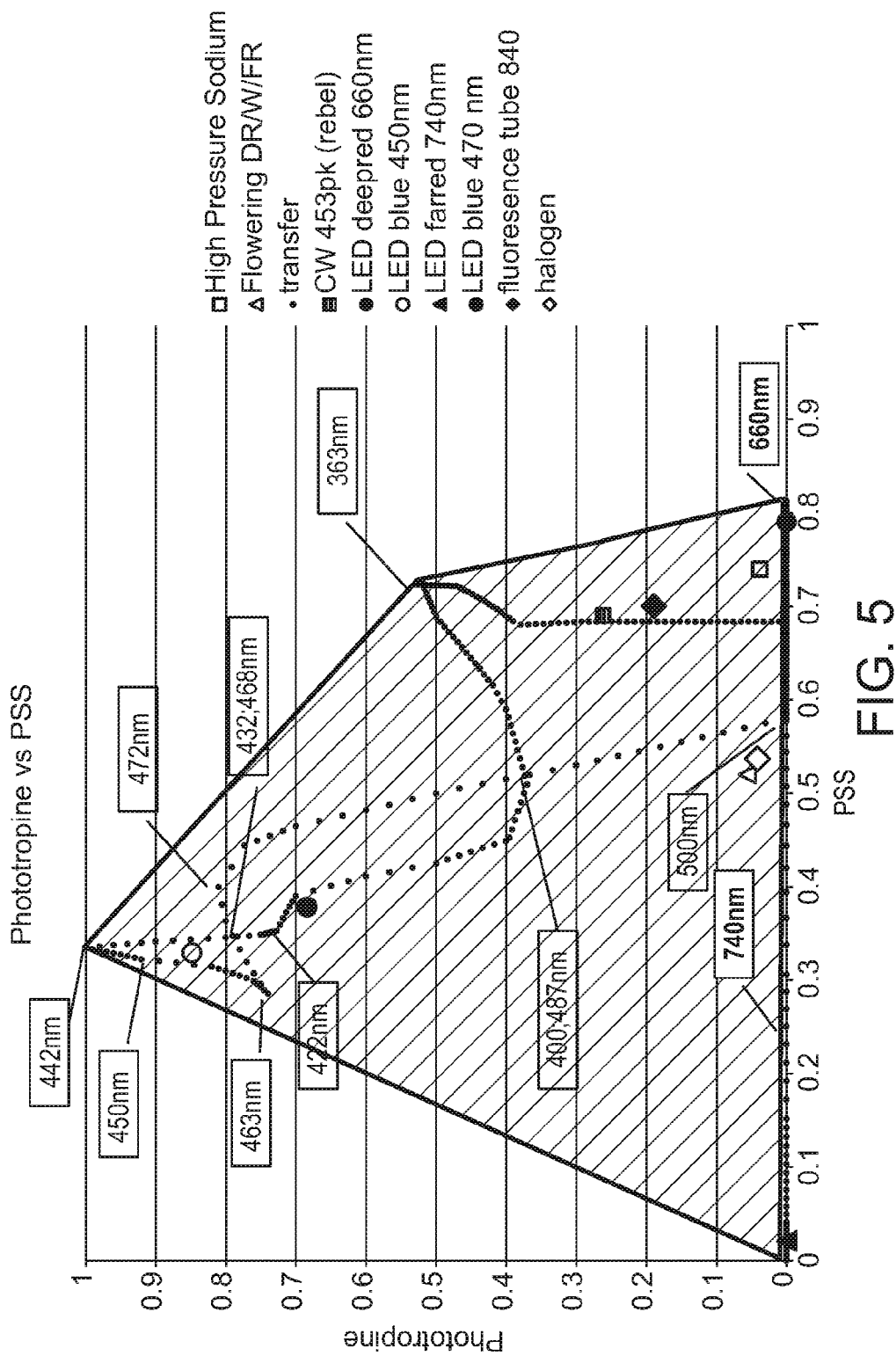
Figure 6:
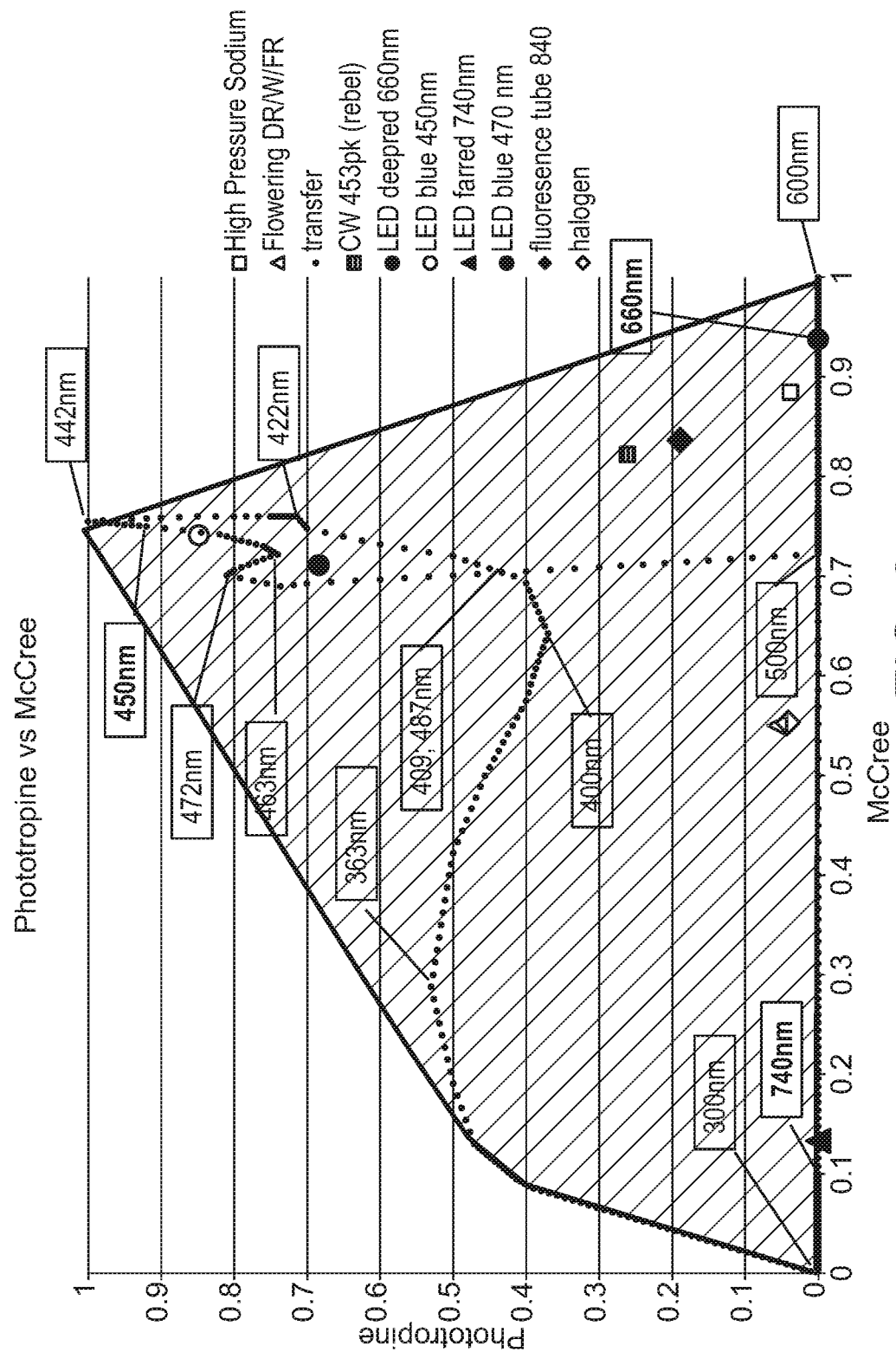

First, FIGS. 4-6 are provided in order to give plant physiologists more insight in the nature of the horticulture action space. In these plots or graphs, several light sources are plotted. The axis are chosen to be able for persons skilled in the field to evaluate possible action space dimensions against their knowledge. For instance, the PSS value is plotted. This PSS value is calculated as defined above. Furthermore, a parameter indicated with "McCree" is plotted. This in fact is the Y value, but normalized to 1. This value thus provides a relative measure for the amount of photosynthesis. A parameter "Phototropine" is also plotted. This value in fact is the Z value defined above, again normalized to 1. Furthermore, small dots are plotted which are indicated as "transfer". These dots represent the values of virtual, monochromatic light sources, with a rectangular spectrum with a width of 1 nm. In the graphs, the outlines show the physically possible light sources. Thus, the space outside the outlines cannot be filled with any light source.

In FIG. 4, the McCree values are plotted against PSS for different light sources. In this respect, as defined in literature, PSS=Pr/(Pr+Pfr). FIG. 5 shows the phototropin versus PSS, and FIG. 6 shows phototropin versus McCree. It should be realized that in particular the PSS parameter introduced non-linearity. It is therefore difficult for a skilled person to interpret the distances in the graphs. FIGS. 4-6 give insight in the horticulture action space. It shows different light sources with respect to one another, and their influence on plants.

Figure 7:
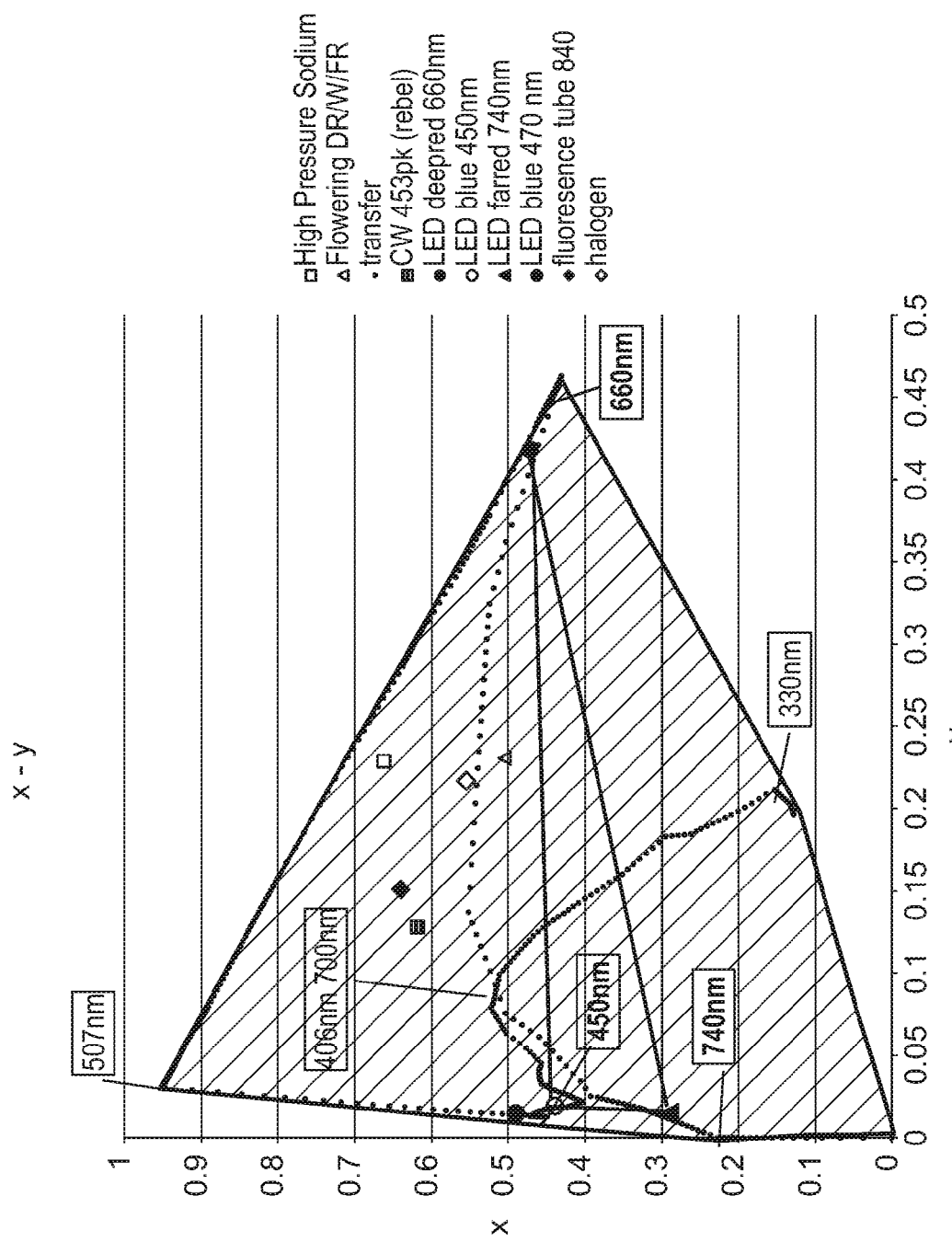
FIGS. 7-9 cross sections of the horticulture action space with View perpendicular on (x,y), (y,z) and (x,z) plane, respectively, again showing positions of the various lighting devices of FIGS. 4-6.
Figure 8:
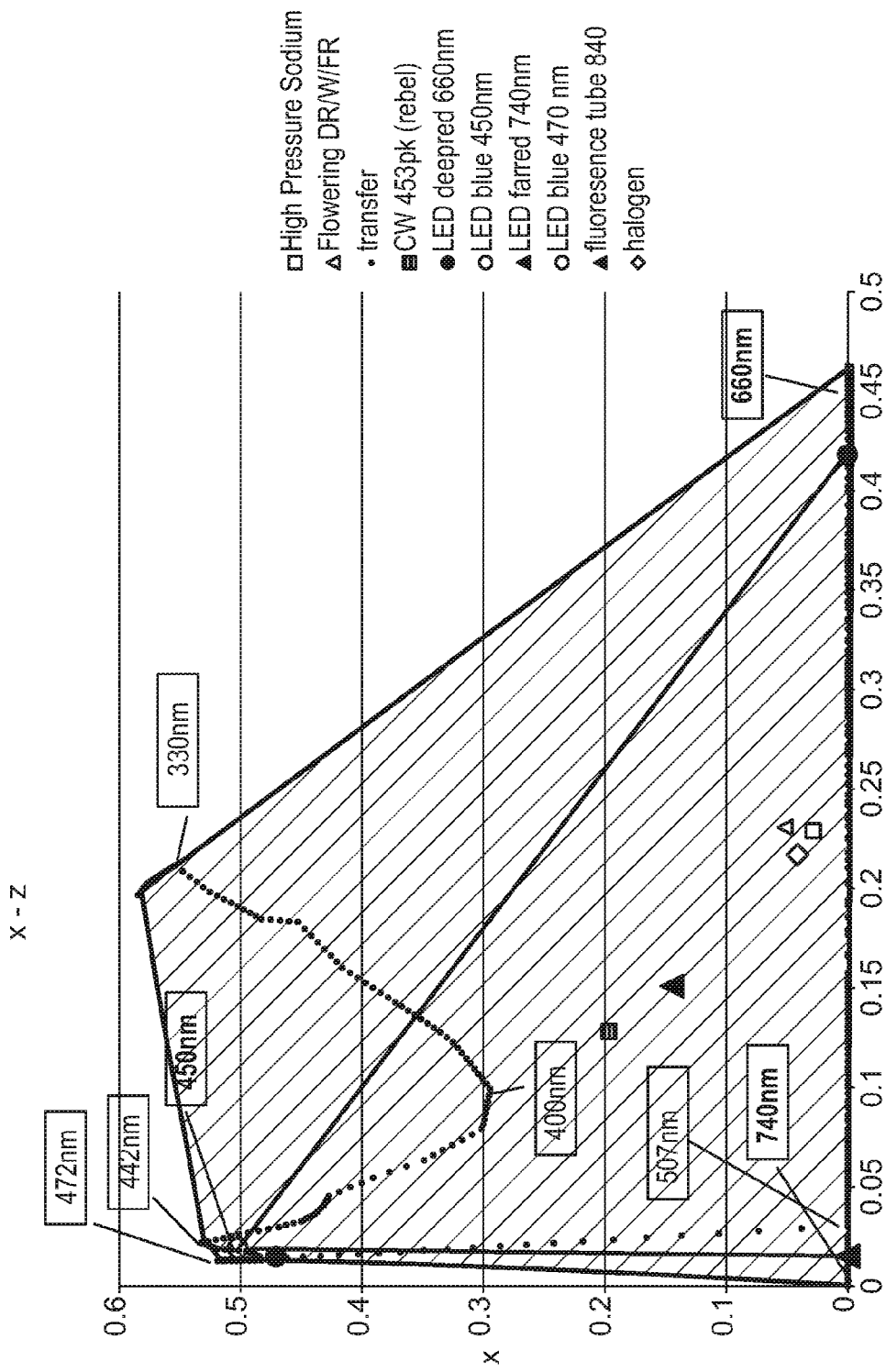
Figure 9:
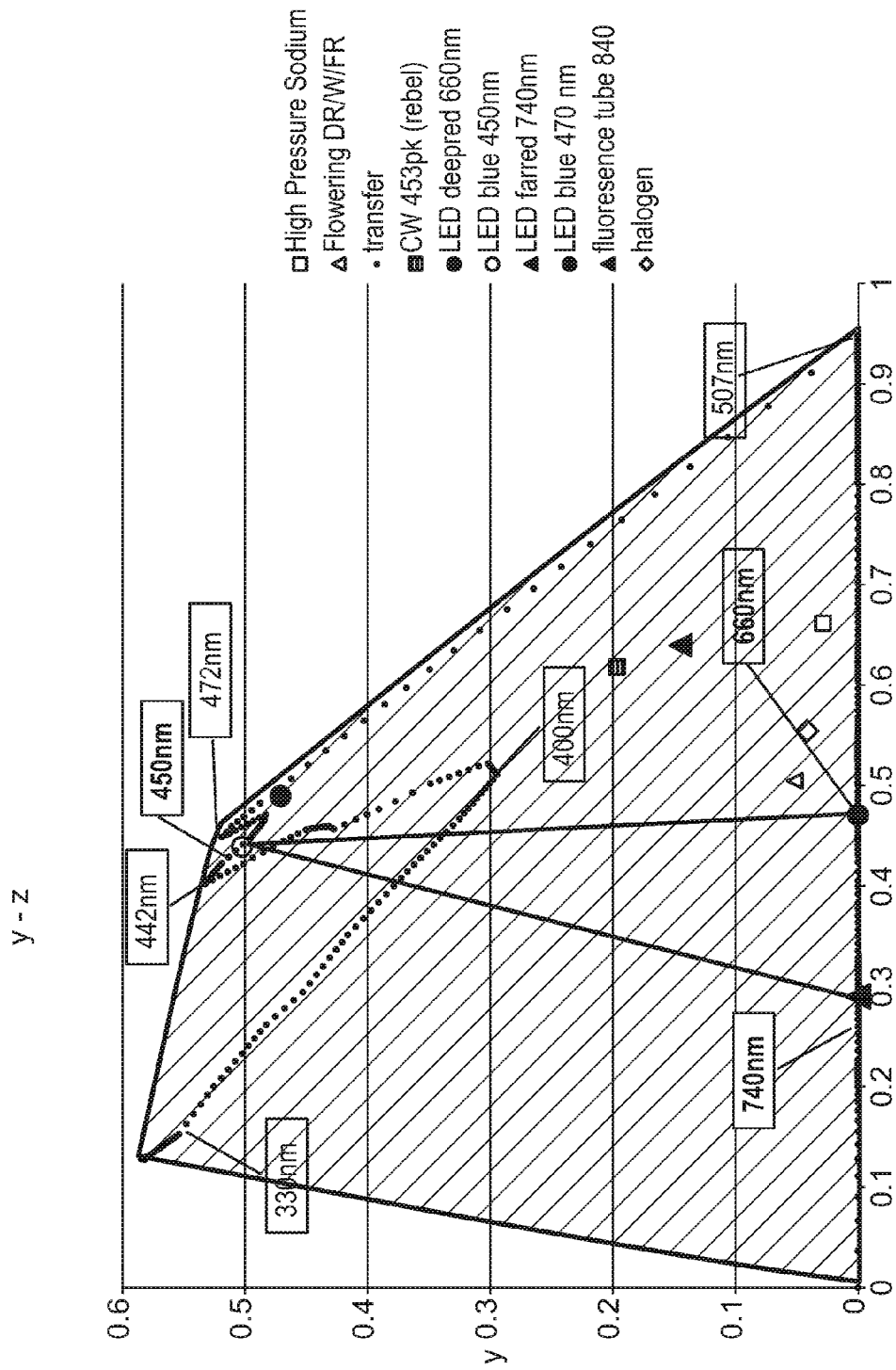

FIGS. 7-9 shows views of the horticulture action space on the x,y-plane, the y, z plane and the x, z plane. In these views, various existing and theoretical lighting devices are plotted. The outlines show all the possible values that can physically be made. Thus, every point inside this area can be produced. Furthermore, various symbols show the horticulture action space coordinates of these lighting devices. As this horticulture action space is normalized, one can relatively simple see the effect of lighting devices. Furthermore, this space is linear. This means that in fact, a line can be drawn between light sources, and any point on this line is a combination of these two light sources. And in fact, all these points represent an effect on plants of the combination of the light sources. Furthermore, the relative position on the line even corresponds to the relative number of light sources. For instance, half way a line between a light source A and a light source B means the effect of combining an equal number of light sources A and B.

In FIGS. 7-9, the small dots again show the effect of monochromatic light sources in the horticulture action space, the same as in FIGS. 4-6.

In this example, consider lighting devices that are indicated "LED deepred 660 nm", "LED farred 740 nm" and "LED blue 450 nm" in FIGS. 7-9. These lighting devices are in fact nearly monochromatic sources. Lines now connect these different lighting devices. These lines in fact bound a triangle in the (x,y) plane. Using these three lighting devices, all the points in this triangle, including the lines, can be realized. In fact, the definition of the horticulture action space is such that the position in and on the triangle corresponds to absolute ratios of the lighting devices. Thus, for instance the position halfway the line connecting "LED blue 450 nm" and "LED deepred 660 nm" correspond with using these lighting devices in a 1:1 ratio, relative to their absolute output in.

Figure 10:
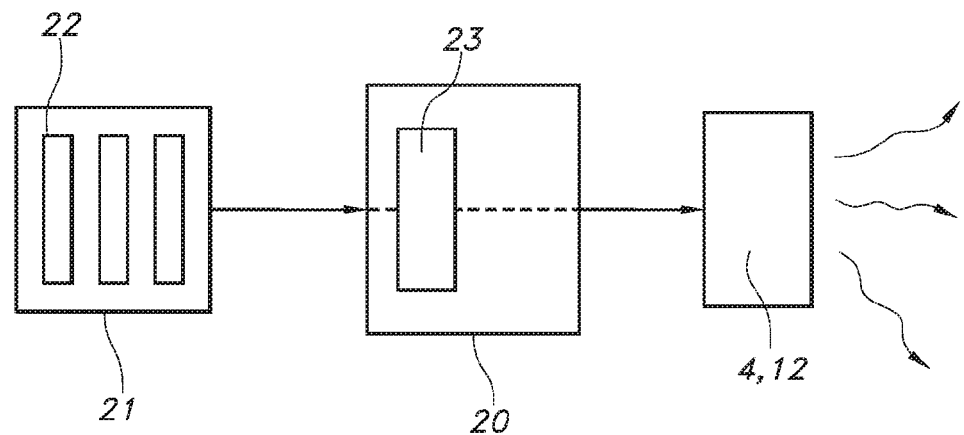
FIGS. 10-15 show several examples of implementations of the interface, with FIG. 10 showing a basic configuration of the interface functionally coupled to a lighting system.
Figure 11:
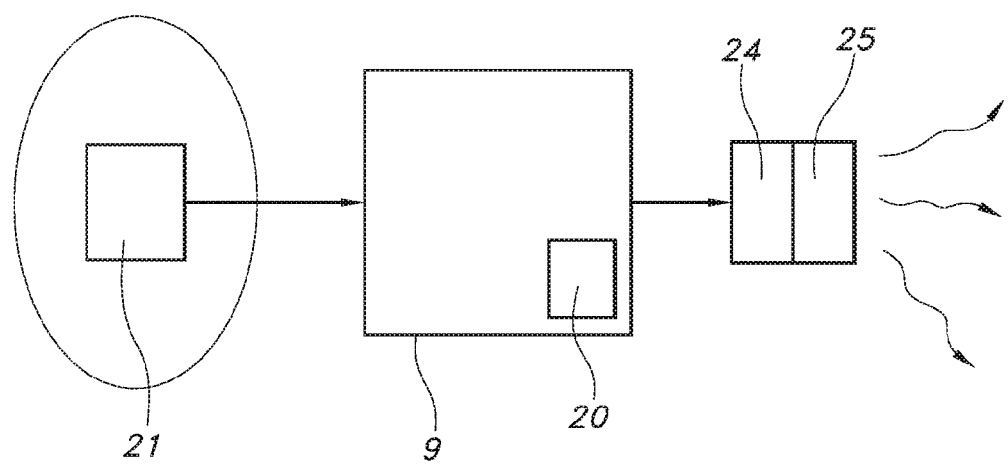
Figure 12:
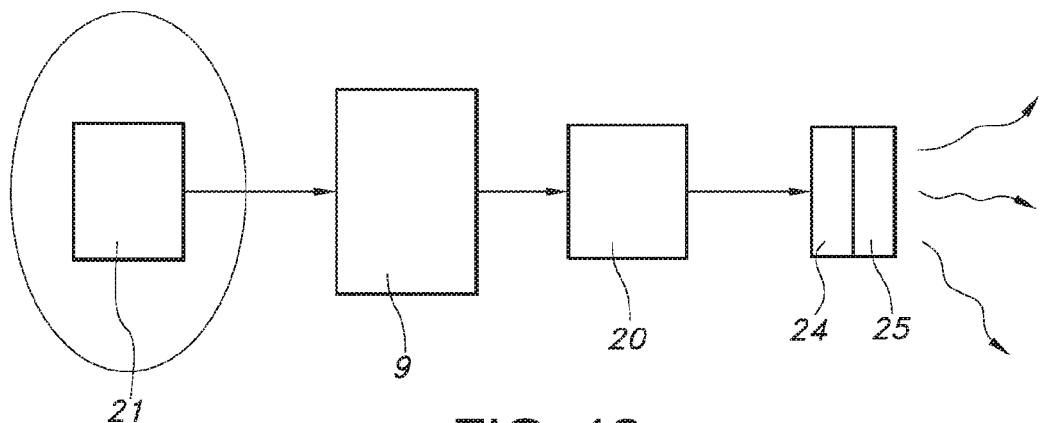
Figure 13:
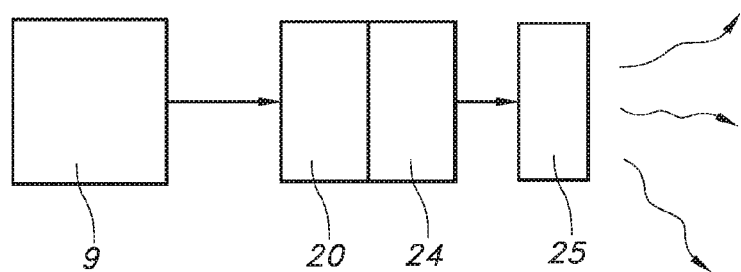
Figure 14:
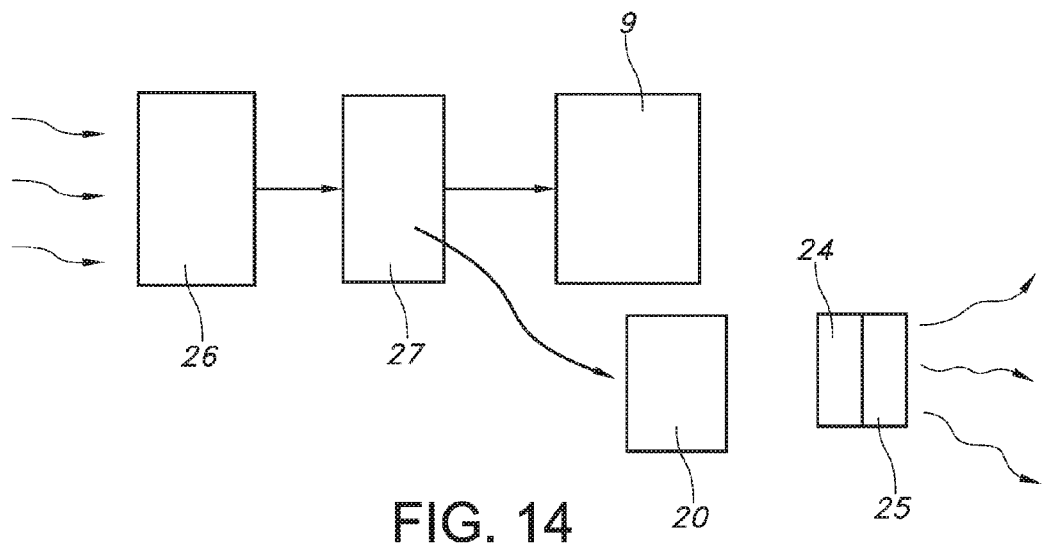
Figure 15:
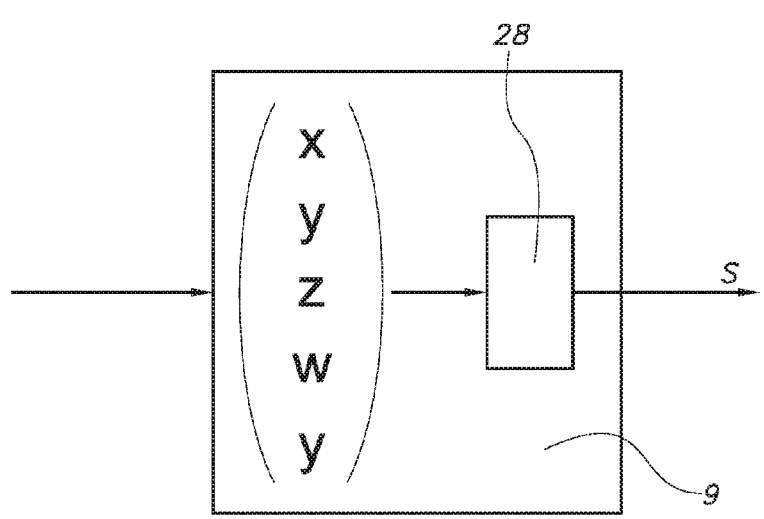

In FIGS. 10-15, several possible implementations of the interface are illustrated in schematic drawings. FIG. 10 shows a basic configuration of the interface 20 functionally coupled to a lighting system 4, 12. FIG. 11 shows the interface 20 implemented in a climate computer 9 in a greenhouse. FIG. 12 shows the interface 20 separate from the climate computer 9. FIG. 13 shows the interface 20 implemented in a lighting control device 24. FIG. 14 shows an embodiment of the interface 20 implemented in a sensor. FIG. 15 shows an embodiment of a basic configuration of an interface with a lighting system interface part.

In the embodiment of FIG. 10, interface 20 comprises a light recipe interface part 23. The light recipe interface part 23 is adapted for receiving a light recipe. Such a light recipe comprises at least one target point in a horticulture action space. The target point in the horticulture action space defines a desired physiological plant response. The interface 20 is at its input end functionally coupled to a light recipe database 21 that contains one or more light recipes 22. At its output end, the interface 20 is functionally coupled to one or more lighting systems 4, 12. In this respect, the interface 20 will often be coupled via a wired or wireless connection.

In the embodiment of FIG. 11, the interface 20 is installed in the climate computer 9. The interface 20 may be completely integrated into climate control software running on the climate computer 9. Alternatively, the interface 20 may be incorporated into ad add-in, or an apps, that exchange data with the climate control software. The climate computer 9 is functionally coupled to a lighting system 4, 12, here comprising one or more light emitting sources 25 and a lighting controller 24. Such a lighting controller 24 is here integrated into the light emitting sources, but other implementations may be possible.

In an embodiment of FIG. 12, the interface 20 is implemented separate from the climate computer 9. In this embodiment, climate computer 9 is functionally coupled to a remote light recipe database 21. The climate computer 9 is functionally coupled to interface 20. Interface 20, in turn, is functionally coupled tone or more lighting systems, schematically indicated, having one or more light sources 25 and a lighting controller 24. In fact, in this embodiment, interface 20 is functionally coupled to the lighting controller 24.

In FIG. 13, an embodiment is indicated in which the interface 20 is in fact integrated with the lighting controller 24. In an embodiment, the share one common housing.

In FIG. 14, interface 20 is functionally coupled to a sensor for measuring one or more illumination parameter. In fact, this embodiment is one of many possible embodiments. In this embodiment, detector 26 for detecting ambient light radiation is functionally coupled to a processing part 27. The detector 26 provides for instance a signal representative of at least the light intensity. Often, such a signal comprises intensity as a function of wavelength: $I(\lambda)$.

In a state of the art sensor, the output signal can be provided to a climate computer 9. In this embodiment, detector 26 is functionally coupled to processing device 27 for providing wavelength-based intensity data. This data is provided to climate computer 9. In this embodiment, processing device 27 is also functionally coupled to interface 20. Interface 20 may further be functionally coupled to climate computer 9 and to lighting system 4, 12.

In FIG. 15, another embodiment of interface 20 is illustrated. In this embodiment, interface 20 is provided with lighting system interface part 28. Lighting interface part 28 receives horticulture action space coordinates and outputs a control signal S for controlling a lighting controller (not shown).

EXAMPLE

An example of the use of a light recipe is in the growth of tulips as cut-flowers. In this example, growth taken place in a greenhouse in three layers. Growth takes place between weeks 46 and 15 in a northern hemisphere environment in a greenhouse.

Light sources are LED production modules having either white LEDs or blue LEDs in combination with red LEDs.

|  | Unit #1 red with white LEDs | Unit #2 red with blue LEDs |
|---|---|---|
| total power(normal 1 W) | 0.9981 | 1.0001 |
| PSS (=X/(W + X)) | 0.76 | 0.78 |
| McCree (Y) | 0.89 | 0.90 |
| Photropine (Z) | 0.11 | 0.11 |
| X | 0.32 | 0.36 |
| Y | 0.52 | 0.48 |
| Z | 0.065 | 0.058 |
| nr of photons farred (700-80 nm) | 0.065 | 0.014 |
| Nr of photons red (600-700 nm) | 3.67 | 4.61 |
| nr of photons PAR (400-700 nm) | 5.02 | 5.23 |
| nr of photons blue (400-500 nm) | 0.50 | 0.60 |

For unit #1: 5.0 μmol photons is 1 W optical power and an Y of 0.89/m$^2$
For unit #2: 5.2 μmol photons is 1 W optical power and an Y of 0.9/m$^2$ Interesting to see is that the PSS, Y and Z values are almost the same for both lamp types. This therefore means that the effect on the plants are the same and these two devices are interchangeable although the spectral composition is totally different.

Thus:

15-30 μmol/s/m$^2$ for unit #1=3.0-6.0 W optical power/m$^2$, an Y-value of 2.67-5.34, and a horticulture action point of (0.32, 0.52, 0.064).

15-30 μmol/s/m$^2$ for unit #2=2.9-5.8 W optical power/m$^2$, an Y-value of 2.61-5.22, and a horticulture action point of (0.36, 0.47, 0.058);

Both units have a different horticulture action point, but PSS values and phototropine action are comparable under comparable light intensity. Thus, plant response will be comparable. The difference may be that unit #1 is less energy efficient, thus requiring a larger installed power.

Light sources with the same color point and Y-value have the same effect on plant growth so are comparable, but other factors as better color rendering (for human eye) needed for the grower to monitor plant health, or power consumption of the lamp and price can now be compared.

In this case, a light recipe may be:

Day 0-7: (x, y, x)=(0.36, 0.47, 0.058) and Y=1.36 or (x, y, z)=(0.32, 0.52, 0.064) and Y=1.56;

Day 8-14 Sunlight;

Day 15-21 (x, y, z)=(0.36, 0.47, 0.058) and Y=2.72 or (x, y, z)=(0.32, 0.52, 0.064) and Y=3.12.

Calculation of Photon Flux:

$$n(\text{total})[\mu\text{mol}] = 1.10^{-6} \cdot \int_{300\,nm}^{800\,nm} I(\lambda) \cdot \frac{\lambda}{N_A \cdot h \cdot c} d\lambda$$

$$n(PAR)[\mu\text{mol}] = 1.10^{-6} \cdot \int_{400\,nm}^{700\,nm} I(\lambda) \cdot \frac{\lambda}{N_A \cdot h \cdot c} d\lambda$$

$$n(\text{farred})[\mu\text{mol}] = 1.10^{-6} \cdot \int_{700\,nm}^{800\,nm} I(\lambda) \cdot \frac{\lambda}{N_A \cdot h \cdot c} d\lambda$$

$$n(\text{red})[\mu\text{mol}] = 1.10^{-6} \cdot \int_{600\,nm}^{700\,nm} I(\lambda) \cdot \frac{\lambda}{N_A \cdot h \cdot c} d\lambda$$

$$n(\text{blue})[\mu\text{mol}] = 1.10^{-6} \cdot \int_{400\,nm}^{500\,nm} I(\lambda) \cdot \frac{\lambda}{N_A \cdot h \cdot c} d\lambda$$

($N_A$ = Avogadro number;

$h$ = Planck's constant; $c$ is speed of light)

It will also be clear that the above description and drawings are included to illustrate some embodiments of the invention, and not to limit the scope of protection. Starting from this disclosure, many more embodiments will be evident to a skilled person which are within the scope of protection and the essence of this invention and which are obvious combinations of prior art techniques and the disclosure of this patent.

The invention claimed is:

1. An interface for converting a desired physiological plant response into control instructions for at least one lighting system having at least adjustable lighting property, said interface comprising:
   a receiver for receiving a desired physiological plant response;
   a processor functionally coupled to said receiver for converting said desired physiological plant response into said control instructions, and
   a transmitter, functionally coupled to said processor, for transmitting said control instructions,
wherein said desired physiological plant response is defined as a set point in a multi-dimensional horticulture action space, said multi-dimensional horticulture action space being represented by at least two dimensions selected from a first dimension representative for a desired photosynthesis action, a second dimension representative for a desired phototropine action, a third dimension representative for a desired phytochrome Pr action, and a fourth dimension representative for a desired phytochrome Pfr action,
wherein said processor is functionally coupled to a memory comprising a description of a subspace of the multi-dimensional horticulture action space representing points in the multi-dimensional horticulture action space that are convertible into control instructions executable by a lighting system, and
wherein said processor is adapted for mapping said set point to a target point in said subspace and determine corresponding control instructions for a lighting system.

2. The interface of claim 1, wherein said desired physiological plant response is defined as a set point in a multi-dimensional horticulture action space, said multi-dimensional horticulture action space being represented by one of
   (i) a first coordinate system comprising at least a first dimension representative for a desired photosynthesis action and a second dimension representative for a desired phototropine action;
   (ii) a second coordinate system comprising at least a first dimension representative for a desired photosynthesis action, a second dimension representative for a desired phytochrome Pr action and third dimension representative for a desired phytochrome Pfr action; and
   (iii) a third coordinate system comprising at least a first dimension representative for a desired phototropine action, a second dimension representative for a desired phytochrome Pr action and third dimension representative for a desired phytochrome Pfr action.

3. The interface of claim 1, wherein said processor is adapted to map said set point in said subspace based on at least one optimizing criterion.

4. The interface of claim 1, wherein said multi-dimensional horticulture action space comprises at least a first dimension representative for a desired photosynthesis action, a second dimension representative for a desired phototropine action, a third dimension representative for a desired phytochrome Pr action, and a fourth dimension representative for a desired phytochrome Pfr action.

5. The interface of claim 1, wherein said multi-dimensional horticulture action space comprises a further dimension, said further dimension representative for a desired stomata opening action.

6. The interface of claim 5, wherein said receiver is further adapted to receive a horticulture light recipe comprising at least a label for identifying a type of plant, at least one desired physiological plant response, and a time schedule for said at least one desired physiological plant response, with said at least one desired physiological plant response represented as at least one horticulture action coordinate.

7. The interface of claim 6, wherein said receiver is further adapted for receiving a lighting system definition comprising a lighting system identification with associated control instructions for executing physiological plant responses defined as points defining said sub space in said multi-dimensional horticulture action space, and which control instructions are executable by said lighting system, and said receiver is adapted for providing a lighting system definition to said memory.

8. The interface of claim 7, wherein said receiver is further adapted for receiving a sensor value representative for a sensed light spectrum, and wherein the processor is further adapted for mapping said sensor value to a sensed point in said multi-dimensional horticulture action space.

9. The interface of claim 1, further comprising a display, functionally coupled to said processor, for displaying the sub space of said at least one light system relative to the horticulture action space, or for displaying projections thereof, preferably the display additionally displays at least one of said set point and said target point relative to said sub space, of projections thereof.

10. A horticulture system, comprising a horticulture lighting interface of claim 1, at least one lighting system, and a climate control system, wherein the interface is functionally coupled with a climate control system for providing at least one desired physiological plant response to said interface and further functionally coupled with a lighting system for receiving control instructions from said interface and to provide light mapped to said at least one desired physiological plant response.

11. A horticulture system, comprising the horticulture lighting interface of claim 1, and a horticulture light recipe management system, adapted to provide a horticulture light recipe comprising at least a label for identifying a type of plant, at least one desired physiological plant response defined as at least one set point in said multi-dimensional horticulture action space, a time schedule for said at least one desired physiological plant response, wherein said interface is functionally coupled to said horticulture light recipe management system for receiving said horticulture light recipe.

12. A horticulture system comprising the horticulture lighting interface of claim 1, further comprising a lighting management system comprising a repository of lighting system definitions each comprising a lighting system identification with associated control instructions for executing physiological plant responses defined as points defining said sub space in said multi-dimensional horticulture action space, and wherein said interface is functionally coupled to said lighting management system for accessing said repository.

13. A sensor for providing a sensor value representative for a sensed light spectrum, wherein said sensor is functionally coupled to a sensor interface for converting said sensor value into an estimated physiological plant response, said sensor interface comprising:
   a receiver for receiving a sensor value;
   a processor functionally coupled to said receiver for converting said sensor value into said estimated physiological plant response, and a transmitter, functionally coupled to said processor for transmitting said estimated physiological plant response, wherein said estimated physiological plant response is defined as an estimation point in a multi-dimensional horticulture action space, said multi-dimensional horticulture action space being represented by one of
  (i) a first coordinate system comprising at least a first dimension representative for a desired photosynthesis action and a second dimension representative for a desired phototropine action;
  (ii) a second coordinate system comprising at least a first dimension representative for a desired photosynthesis action, a second dimension representative for a desired phytochrome Pr action and third dimension representative for a desired phytochrome Pfr action; and
  (iii) a third coordinate system comprising at least a first dimension representative for a desired phototropine action, a second dimension representative for a desired phytochrome Pr action and third dimension representative for a desired phytochrome Pfr action;

wherein said processor is adapted for mapping said sensor value to said estimation point.

14. A method for converting a desired physiological plant response into control instructions for at least one lighting system having at least one adjustable lighting property, said method comprising:
  receiving a desired physiological plant response, wherein said desired physiological plant response is defined as a set point in a multi-dimensional horticulture action space, said multi-dimensional horticulture action space being represented by one of
  (i) a first coordinate system comprising at least a first dimension representative for a desired photosynthesis action and a second dimension representative for a desired phototropine action;
  (ii) a second coordinate system comprising at least a first dimension representative for a desired photosynthesis action, a second dimension representative for a desired phytochrome Pr action and third dimension representative for a desired phytochrome Pfr action; and
  (iii) a third coordinate system comprising at least a first dimension representative for a desired phototropine action, a second dimension representative for a desired phytochrome Pr action and third dimension representative for a desired phytochrome Pfr action;
  converting said desired physiological plant response into control instructions, the converting comprising mapping said set point to a target point in a subspace of the multi-dimensional horticulture action space and determining corresponding control instructions for said at least one lighting system, wherein said subspace comprises points in the multi-dimensional horticulture action space that are convertible into control instructions for said at least one lighting system and executable by said at least one lighting system; and
  transmitting said control instructions to said at least one lighting system.

* * * * *